US012565477B2

United States Patent

Wang et al.

(10) Patent No.: US 12,565,477 B2
(45) Date of Patent: Mar. 3, 2026

(54) PREPARATION METHOD FOR CHLORINATED COMPOUND

(71) Applicant: JIANGSU KANION PHARMACEUTICAL CO., LTD., Suzhou (CN)

(72) Inventors: Jianfei Wang, Shanghai (CN); Yang Zhang, Shanghai (CN); Shuhui Chen, Shanghai (CN)

(73) Assignee: JIANGSU KANION PHARMACEUTICAL CO., LTD., Jiangsu (CN)

( * ) Notice: Subject to any disclaimer, the term of this patent is extended or adjusted under 35 U.S.C. 154(b) by 622 days.

(21) Appl. No.: 18/000,939

(22) PCT Filed: Jun. 10, 2021

(86) PCT No.: PCT/CN2021/099336

§ 371 (c)(1),
(2) Date: Feb. 17, 2023

(87) PCT Pub. No.: WO2021/249468

PCT Pub. Date: Dec. 16, 2021

(65) Prior Publication Data

US 2023/0219902 A1 Jul. 13, 2023

(30) Foreign Application Priority Data

Jun. 11, 2020 (CN) ........................ 202010528778.5

(51) Int. Cl.
*C07D 249/12* (2006.01)

(52) U.S. Cl.
CPC .................................. *C07D 249/12* (2013.01)

(58) Field of Classification Search
CPC .................................................... C07D 249/12
See application file for complete search history.

(56) References Cited

U.S. PATENT DOCUMENTS

| | | | |
|---|---|---|---|
| 10,633,351 B2 | 4/2020 | Wang et al. |
| 11,352,331 B2 | 6/2022 | Wang et al. |
| 2020/0062720 A1 | 2/2020 | Li et al. |

FOREIGN PATENT DOCUMENTS

| | | | |
|---|---|---|---|
| CN | 103524440 A | 1/2014 |
| CN | 104529848 A | 4/2015 |
| CN | 105263913 A | 1/2016 |
| CN | 108947919 A | 12/2018 |
| WO | 2017215589 A1 | 12/2017 |
| WO | 2019114838 A1 | 6/2019 |

OTHER PUBLICATIONS

Sep. 2, 2021 International Search Report issued in International Patent Application No. PCT/CN2021/099226.

Sep. 2, 2021 Written Opinion of the International Searching Authority issued in International Patent Application No. PCT/CN2021/099336.

Jia, HW. et al."Design, synthesis, and nematicidal activities of novel1,3-thiazin(thiazol)-4 one derivatives against Meloidogyne incognita" Journal of Chemical Research,vol. 43No.5-6 Dec. 31, 2019(Dec. 31, 2019) pp. 161-169.

Jun. 12, 2024 European Extended Search Report issued in Eurasian Patent Application No. 21823032.4.

Aug. 24, 2024 Chinese Office Action issued in Chinese Patent Application No. 202180041874X.

Identification of Thiazolo[5,4-D]Pyrimidine Derivatives as Potent Antiproliferative Agents Through The Drug Repurposing Strategy, European Journal of Medicinal Chemistry 135 (2017) 204-212.

Facile and Versatile Synthesis of Alkyl and Aryl Isothiocyanates by Using Triphosgene and Cosolvent, Synthetic Communications (2013),43(24),3342-3351.

A One-Pot Preparation of Cyanamide From Dithiocarbamate Using Molecular Iodine, Green Chemistry(2009), 11(10), 1503-1506.

On the Efficacy of Anthracene Isomers for Triplet Transmission From Cdse Nanocrystals, Chemical Communications (2017),53(7), 1241-1244.

*Primary Examiner* — Shawquia Jackson
(74) *Attorney, Agent, or Firm* — Houston Beshining Law Office PLLC; Liangang Ye

(57) ABSTRACT

Disclosed is a method for preparing a chlorinated compound, and specifically disclosed is a method for preparing a compound represented by formula (I).

(I)

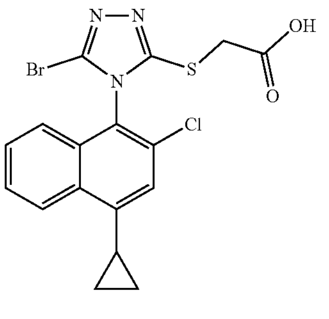

13 Claims, No Drawings

PREPARATION METHOD FOR CHLORINATED COMPOUND

The present application is a National Stage of International Application No. PCT/CN2021/099336 filed on Jun. 10, 2021, which claims priority of the Chinese Patent Application No. CN202010528778.5 filed on Jun. 11, 2020, the contents of which are incorporated herein by reference in their entireties.

TECHNICAL FIELD

The present disclosure relates to a preparation method for a chlorinated compound, and in particular to a preparation method for a compound of formula (I).

BACKGROUND

In recent years, with the changes in people's living habits, the onset of hyperuricemia and gout diseases has shown an upward trend year by year. In Europe and America, epidemiological studies have shown that 1-2% of the general population suffers from gouty arthritis, which is the most common type of arthritis in adult males. Bloomberg estimated that there would be 17.7 million gout patients in 2021. In China, a survey showed that 25.3% of the population aged 20 to 74 has a high blood uric acid level, and 0.36% suffers from gout diseases. At present, clinical therapeutic drugs mainly include: 1) drugs for inhibiting uric acid production, such as xanthine oxidase inhibitors allopurinol and febuxostat; 2) uricosuric drugs, such as probenecid and benzbromarone; and 3) inflammation inhibitors, such as colchicine, and the like. These drugs have certain defects in treatment, and poor efficacy, serious side effects and high cost are some of the main bottlenecks in their clinical application. It has been reported that 40-70% of patients, after receiving standard treatment procedures, did not achieve the expected treatment goal (<6 mg/dL) in blood uric acid level.

URAT1 is an important kidney anion transporter located on the brush border membrane of epithelial cells of renal tubules. It specifically transports uric acid from renal tubules to epithelial cells and is the main driving force for the reabsorption of uric acid in renal tubules. Therefore, if the urate transporter URAT1 is significantly inhibited, the excretion of uric acid in the body can be increased, thereby lowering the blood uric acid level and reducing the possibility of gout attacks.

In December 2015, AstraZeneca's Lesinurad, as shown below, was approved by the U.S. FDA as the first URAT1-targeted inhibitor, and it at a dose of 200 mg/day was approved for use in combination with a xanthine oxidase inhibitor (XOI) (e.g., Febuxostat, etc.) for the treatment of hyperuricemia and gouty arthritis. However, the additional effect of the combined medication was not very significant as compared with the xanthine oxidase inhibitor alone. Meanwhile, Lesinurad at a dose of 400 mg/day was not approved due to the significantly increased toxic side effects observed at high doses (higher incidence of kidney-related adverse events, especially kidney stone), although the combined medication demonstrated a higher additional effect at high doses. Accordingly, the FDA required the Lesinurad label to be filled with a black box warning to warn the medical staff of the risk of acute renal failure caused by Lesinurad, especially when it is not used in combination with XOI, and if an over-approved dose of Lesinurad is used, the risk of renal failure is even higher. Meanwhile, the FDA asked AstraZeneca to continue its investigation on kidney and cardiovascular safety after the launch of Lesinurad. For long-term medication for a metabolic disease, the safety of the drugs is particularly important. Therefore, there is a strong demand in this field to develop a safe drug for lowering blood uric acid level.

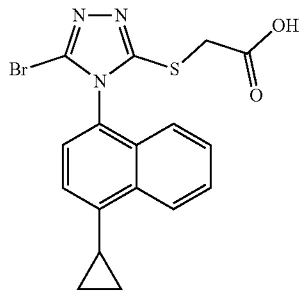

Lesinurad

In the new drug declaration report disclosed by AstraZeneca, the results of the identification experiments of compound Lesinurad in liver microsomes and hepatocyte metabolites of various animal species in vitro were reported in detail. The data showed that M3 and M4, two main metabolites of Lesinurad, were significantly detected in the monkey and human hepatocytes, but M3 and M4 were not detected in dog and rat hepatocytes, as shown in Table-a below.

TABLE a

| System | Species | M3 | M4 | Lesinurad | Total |
|---|---|---|---|---|---|
| Liver microsome | Rat | — | — | 100 | 100 |
| | Dog | — | — | 100 | 100 |
| | Monkey | 7.9 | — | 92.1 | 100 |
| | Human | — | — | 100 | 100 |
| Hepatocyte | Rat | — | — | 100 | 100 |
| | Dog | — | — | 100 | 100 |
| | Monkey | 1.45 | 0.47 | 98.1 | 100 |
| | Human | 2.24 | 5.69 | 92.1 | 100 |

Meanwhile, AstraZeneca also reported the main metabolites and metabolic pathways of Lesinurad after administration in various animal species, among which the dihydroxy metabolite M4 was specifically detected in human metabolites:

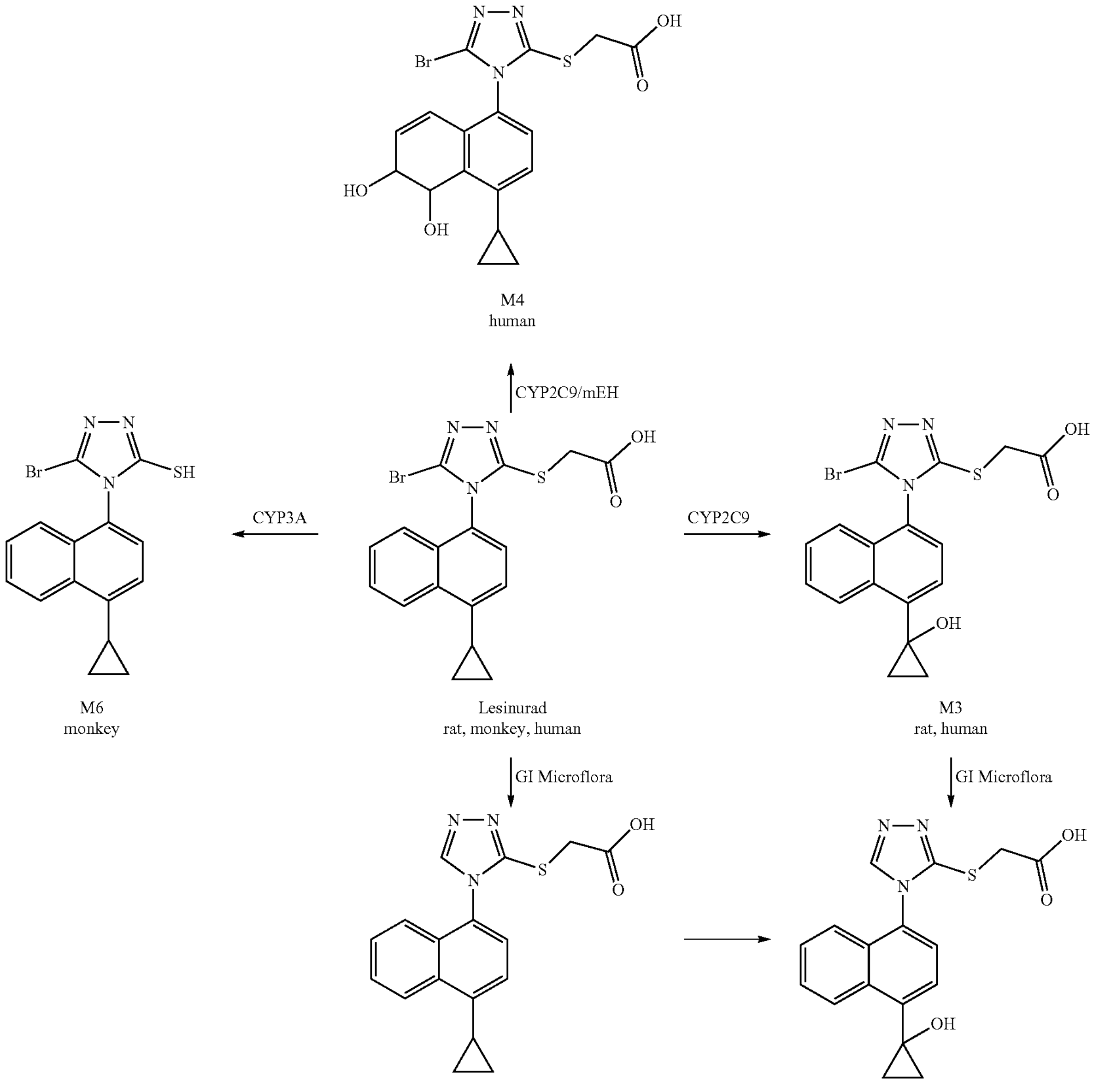

M4
human

M6
monkey

Lesinurad
rat, monkey, human

M3
rat, human

M2
rat, monkey

M5
rat

This was consistent with Lesinurad's clinical data in humans. Experimental data showed that M3 and M4 were the most predominant metabolites found in human clinical trials, as shown in Table-b below.

TABLE-b

| System | Time (h) | Percentage of administered dose | | | | | | | | | | |
|---|---|---|---|---|---|---|---|---|---|---|---|---|
| | | M1 | M2 | M3 | M3b | M4 | M5 | M5b | M16 | Other | Lesinurad | Total |
| Urine | 0-144 | 1.5 | 0.3 | 12.0 | 1.0 | 15.7 | ND | ND | 0.5 | 1.2 | 31.3 | 63.4 |
| Feces | 0-144 | ND | 4.8 | 0.3 | 1.9 | 5.0 | 3.6 | 7.8 | 1.1 | 7.5 | 1.5 | 33.5 |

According to the research, the production pathway of M4 metabolite could be determined as a result of the co-action of cytochrome CYP2C9 and primate epoxide hydrolase mEH. This mEH metabolic pathway was unique to primate species, which explained why no M4 was observed in rats and dogs.

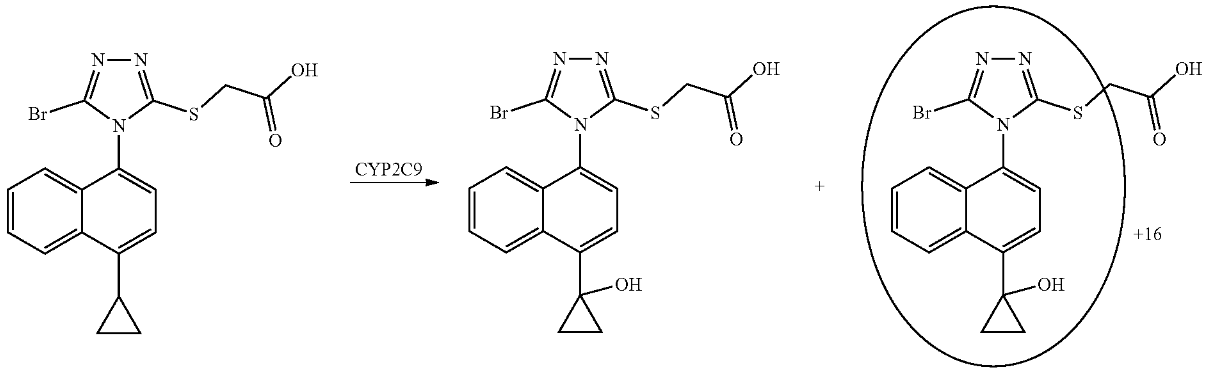

Lesinurad M3 M3a & M3b

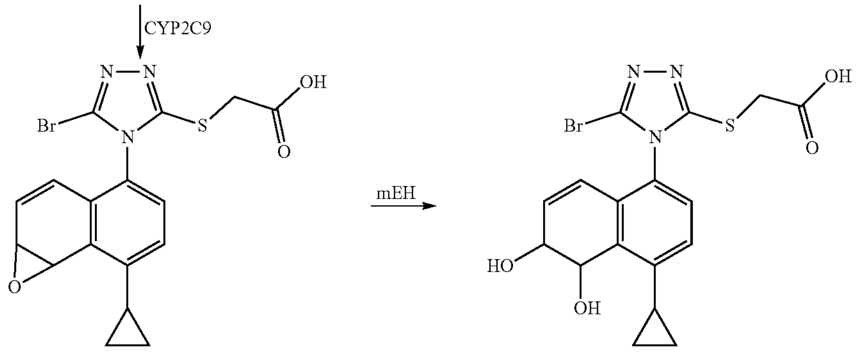

M3c M4

CONTENT OF THE PRESENT INVENTION

The present disclosure provides a preparation method for a compound of formula (I), (I)

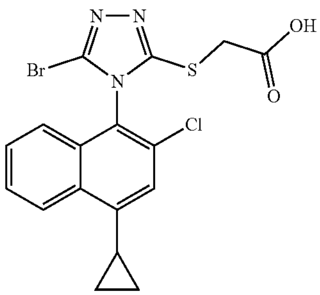

which is characterized by comprising the following step:

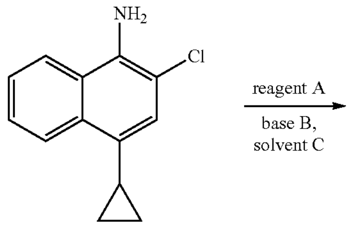

1-2

-continued

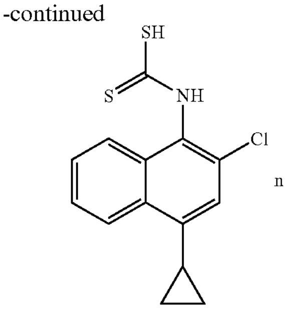

n base B 1-3A wherein, n is selected from 0, 1 and 2;

reagent A is selected from $CS_2$;

base B is selected from TEA, DBU, DIPEA and

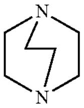

;

and solvent C is selected from a single solvent or a mixed solvent, wherein the single solvent is selected from n-heptane, DMF, acetone and methyl tert-butyl ether, and the mixed solvent is selected from a mixed solvent of acetone and methyl tert-butyl ether.

In some embodiments of the present disclosure, provided is the preparation method, wherein, reagent A is selected from $CS_2$;

base B is selected from

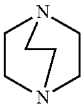

;

and solvent C is selected from a single solvent or a mixed solvent, wherein the single solvent is selected from methyl tert-butyl ether, and the mixed solvent is selected from a mixed solvent of acetone and methyl tert-butyl ether.

In some embodiments of the present disclosure, provided is the preparation method, wherein, reagent A is selected from $CS_2$;

base B is selected from

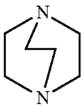

;

and solvent C is selected from a mixed solvent of acetone and methyl tert-butyl ether.

In some embodiments of the present disclosure, provided is the preparation method, wherein reagent A and compound 1-2 are in a molar ratio of (1-6):1, base B and compound 1-2 are in a molar ratio of (2-5):1, and solvent C is a mixed solvent of methyl tert-butyl ether and acetone in a volume ratio of (15-25):1.

In some embodiments of the present disclosure, provided is the preparation method, wherein a temperature of a reaction system is controlled at 0-45° C. in the step of preparing compound 1-3A.

In some embodiments of the present disclosure, provided is the preparation method, wherein the temperature of the reaction system is controlled at 30-35° C. in the step of preparing compound 1-3A.

In some embodiments of the present disclosure, provided is the preparation method, wherein a reaction time is controlled to be 16-60 h in the step of preparing compound 1-3A.

In some embodiments of the present disclosure, the preparation method comprises the following steps:

1-3A

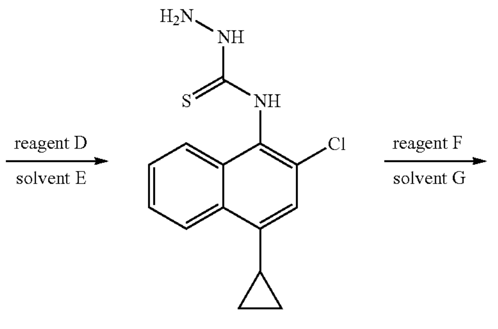

1-4

-continued

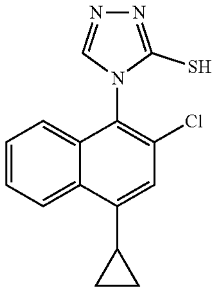

1-5 wherein, reagent D is selected from hydrazine hydrate;

solvent E is selected from EtOH, isopropanol, toluene, MTBE, THF and DMF;

reagent F is selected from DMF-DMA; and solvent G is selected from MTBE, EtOAc, n-heptane, THF, isopropanol and DMF.

In some embodiments of the present disclosure, provided is the preparation method, wherein, reagent D is selected from hydrazine hydrate;

solvent E is selected from EtOH and isopropanol;

reagent F is selected from DMF-DMA; and solvent G is selected from isopropanol.

In some embodiments of the present disclosure, provided is the preparation method, wherein reagent D and compound 1-3A are in a molar ratio of (3-15):1, and reagent F and compound 1-4 are in a molar ratio of (1-3):1.

In some embodiments of the present disclosure, the preparation method comprises the following steps:

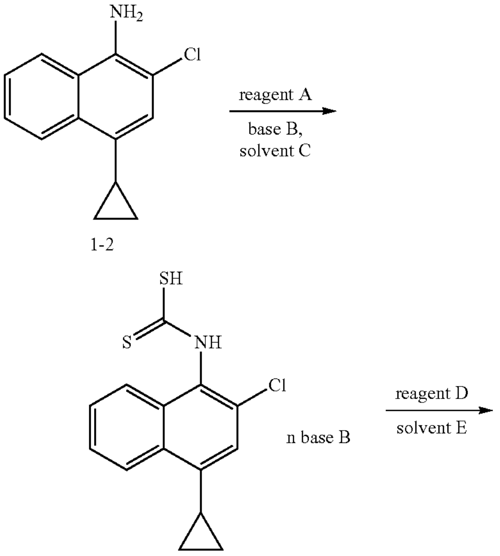

1-2

1-3A

-continued
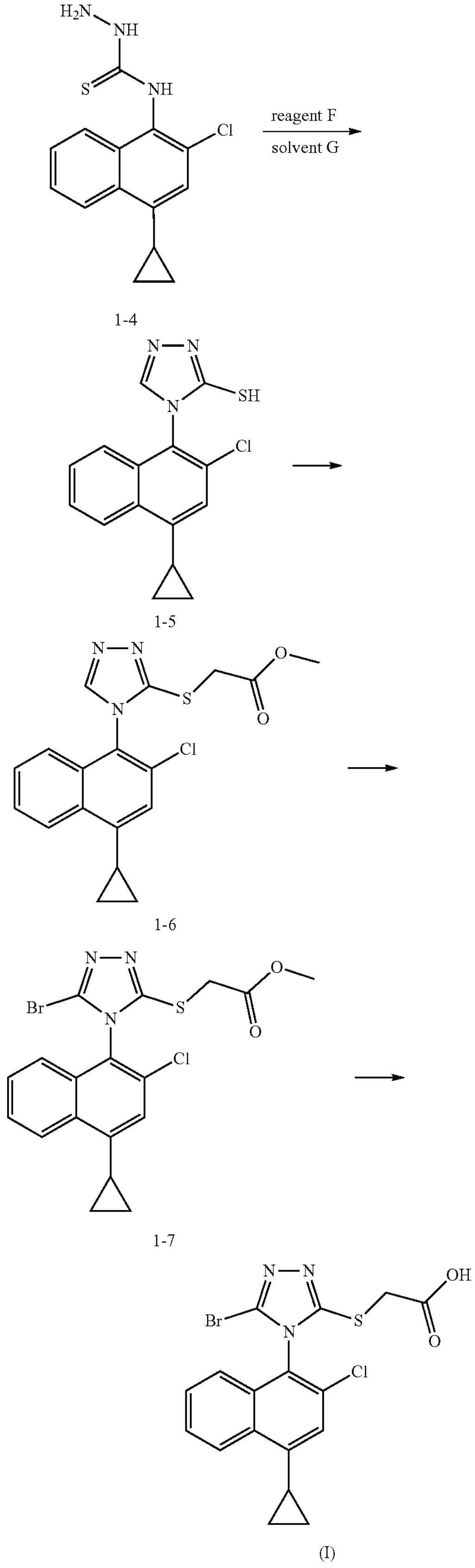
1-4
1-5
1-6
1-7
(I)
wherein,
n is selected from 0, 1 and 2;
reagent A, base B and solvent C are as defined above; and
reagent D, solvent E, reagent F and solvent G are as defined above.
In some embodiments of the present disclosure, the preparation method comprises the following steps:
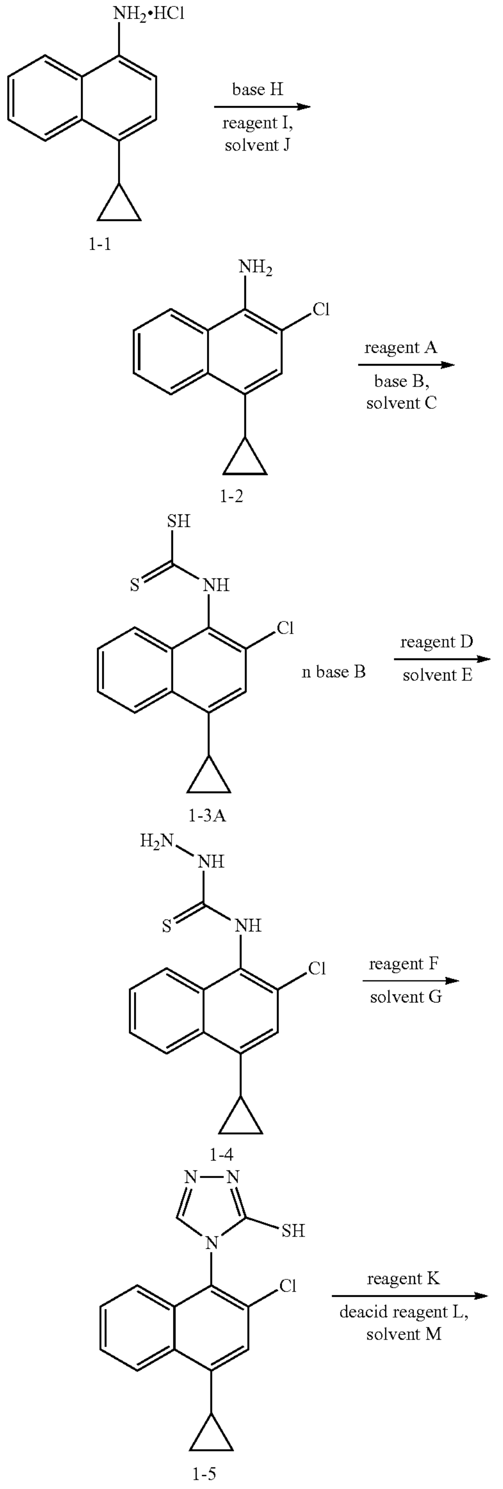
1-1
1-2
1-3A
1-4
1-5

-continued

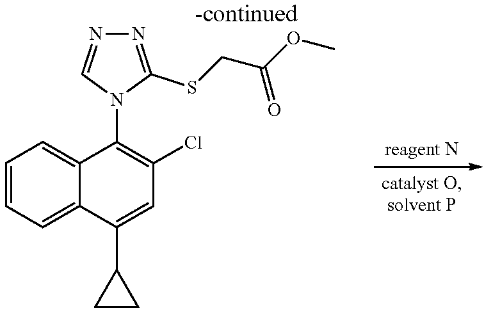

1-6

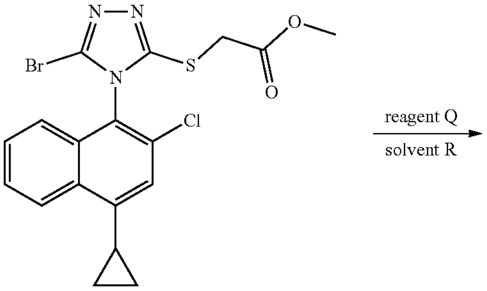

1-7

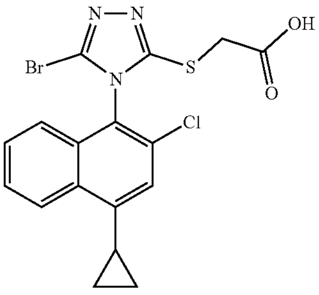

(I)

wherein, n is selected from 0, 1 and 2;

reagent A, base B and solvent C are as defined above;

reagent D, solvent E, reagent F and solvent G are as defined above;

base H is selected from a basic compound;

reagent I is selected from NCS;

solvent J is selected from EtOAc, DCM, PE, THF, MTBE and $CH_3CN$;

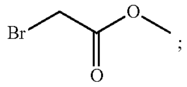

reagent K is selected from deacid reagent L is selected from $K_2CO_3$, $NaHCO_3$, $K_3PO_4$ and NaOAc;

solvent M is selected from EtOAc, DCM, DMF, THF and $CH_3CN$;

reagent N is selected from NBS and dibromohydantoin;

catalyst O is selected from thiocarbonyldiimidazole;

solvent P is selected from THF, $CH_3CN$ and EtOAc;

reagent Q is selected from a base; and solvent R is selected from a mixed solvent, wherein the mixed solvent is selected from a mixed solvent of tetrahydrofuran and water, a mixed solvent of methanol and water, and a mixed solvent of methanol, tetrahydrofuran and water.

In some embodiments of the present disclosure, provided is the preparation method, wherein, reagent A, base B and solvent C are as defined above;

reagent D, solvent E, reagent F and solvent G are as defined above;

base H is selected from NaOH;

reagent I is selected from NCS;

solvent J is selected from EtOAc;

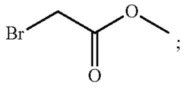

reagent K is selected from deacid reagent L is selected from NaOAc;

solvent M is selected from EtOAc;

reagent N is selected from NBS;

catalyst O is selected from thiocarbonyldiimidazole;

solvent P is selected from EtOAc;

reagent Q is selected from lithium hydroxide monohydrate, lithium hydroxide, sodium hydroxide and potassium hydroxide; and solvent R is selected from a mixed solvent of tetrahydrofuran and pure water in a volume ratio of (0.25-4):1.

The present disclosure provides a preparation method for a compound of formula (I), (I)

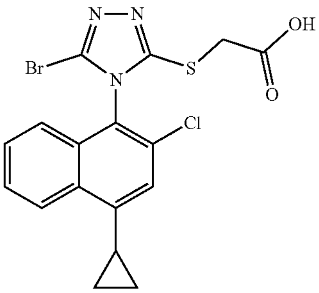

which is characterized by comprising the following step:

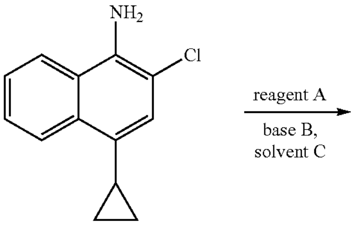

1-2

-continued

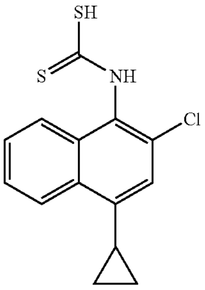

1-3A wherein, reagent A is selected from $CS_2$;

base B is selected from TEA, DBU, DIPEA and

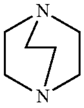

;

and solvent C is selected from a single solvent and a mixed solvent, wherein the single solvent is selected from n-heptane, DMF, acetone and methyl tert-butyl ether, and the mixed solvent is selected from a mixed solvent of acetone and methyl tert-butyl ether.

In some embodiments of the present disclosure, provided is the preparation method, wherein, reagent A is selected from $CS_2$;

base B is selected from

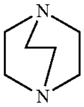

;

and solvent C is selected from a single solvent and a mixed solvent, wherein the single solvent is selected from methyl tert-butyl ether, the mixed solvent is selected from a mixed solvent of acetone and methyl tert-butyl ether, and the other variables are as defined herein.

In some embodiments of the present disclosure, provided is the preparation method, wherein, reagent A is selected from $CS_2$;

base B is selected from

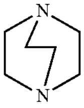

;

and solvent C is selected from a mixed solvent of acetone and methyl tert-butyl ether, and the other variables are as defined herein.

In some embodiments of the present disclosure, provided is the preparation method, wherein reagent A and compound 1-2 are in a molar ratio of (1-6):1, base B and compound 1-2 are in a molar ratio of (2-5):1, solvent C is a mixed solvent of methyl tert-butyl ether and acetone in a volume ratio of (15-25):1, and the other variables are as defined herein.

In some embodiments of the present disclosure, provided is the preparation method, wherein a temperature of a reaction system is controlled at 0-45° C. in the step of preparing compound 1-3A, and the other variables are as defined herein.

In some embodiments of the present disclosure, provided is the preparation method, wherein the temperature of the reaction system is controlled at 30-35° C. in the step of preparing compound 1-3A, and the other variables are as defined herein.

In some embodiments of the present disclosure, provided is the preparation method, wherein a reaction time is controlled to be 16-60 h in the step of preparing compound 1-3A, and the other variables are as defined herein.

In some embodiments of the present disclosure, the preparation method comprises the following steps:

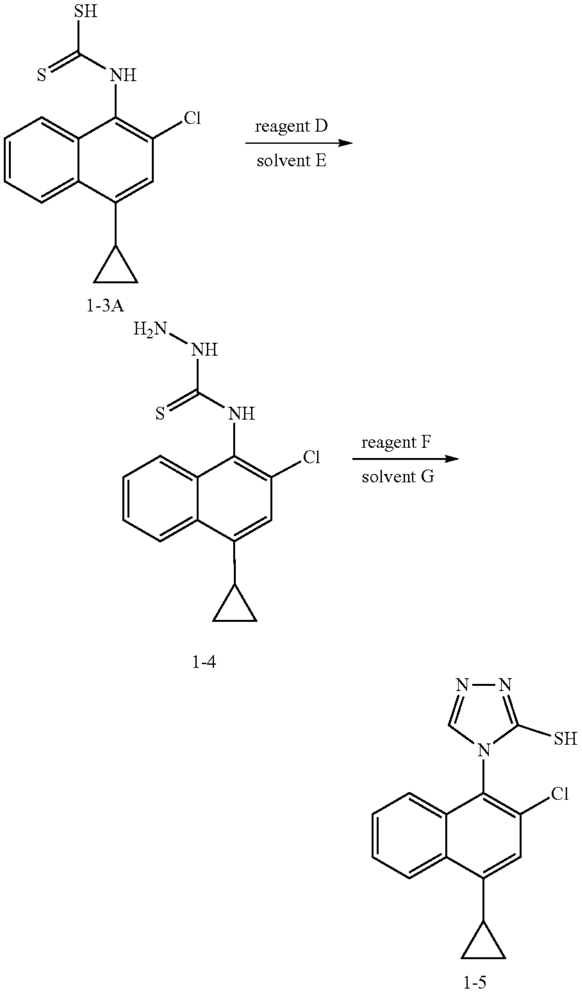

1-3A 1-4

1-5 wherein, reagent D is selected from hydrazine hydrate;

solvent E is selected from EtOH, isopropanol, toluene, MTBE, THF and DMF;

reagent F is selected from DMF-DMA; and solvent G is selected from MTBE, EtOAc, n-heptane, THF, isopropanol and DMF, and the other variables are as defined herein.

In some embodiments of the present disclosure, provided is the preparation method, wherein, reagent D is selected from hydrazine hydrate;

solvent E is selected from EtOH and isopropanol;

reagent F is selected from DMF-DMA; and solvent G is selected from isopropanol, and the other variables are as defined herein.

In some embodiments of the present disclosure, provided is the preparation method, wherein reagent D and compound 1-3A are in a molar ratio of (3-15):1, reagent F and compound 1-4 are in a molar ratio of (1-3):1, and the other variables are as defined herein.

In some embodiments of the present disclosure, the preparation method comprises the following steps:

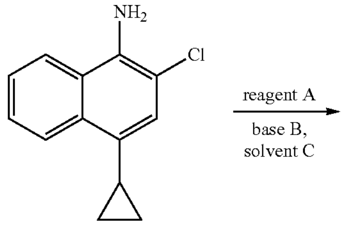

1-2

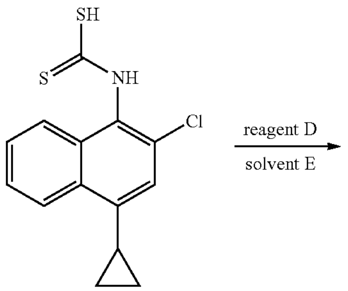

1-3A

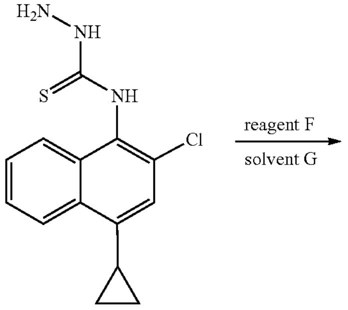

1-4

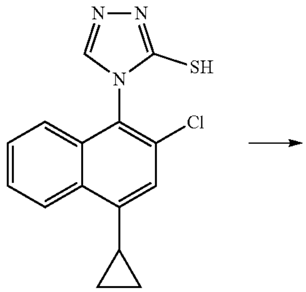

1-5

-continued

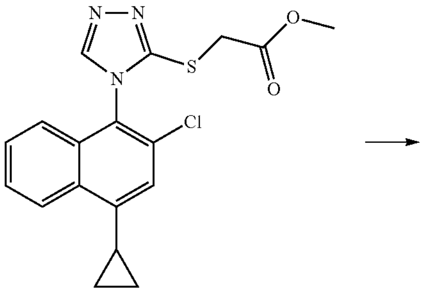

1-6

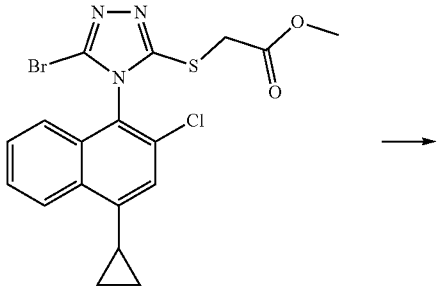

1-7

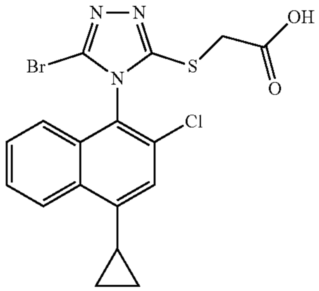

(I)

wherein, reagent A, base B and solvent C are as defined herein; and reagent D, solvent E, reagent F and solvent G are as defined herein, and the other variables are as defined herein.

In some embodiments of the present disclosure, the preparation method comprises the following steps:

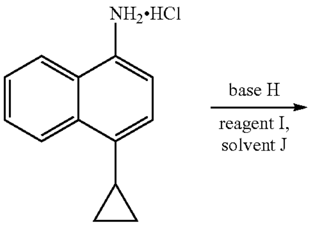

1-1

-continued

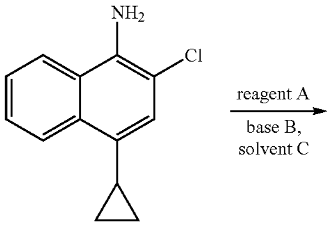

1-2

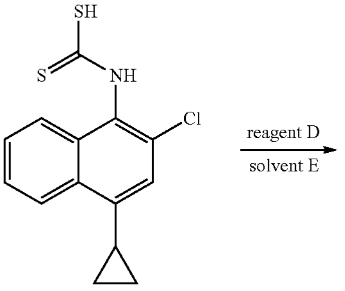

1-3A

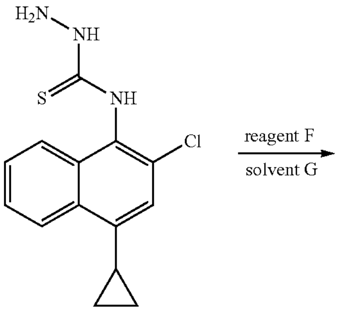

1-4

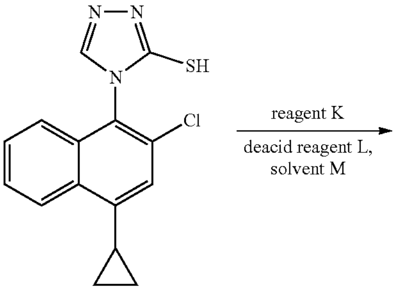

1-5

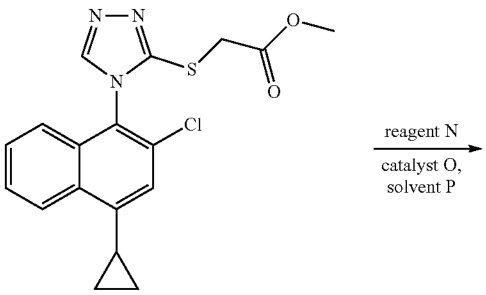

1-6

-continued

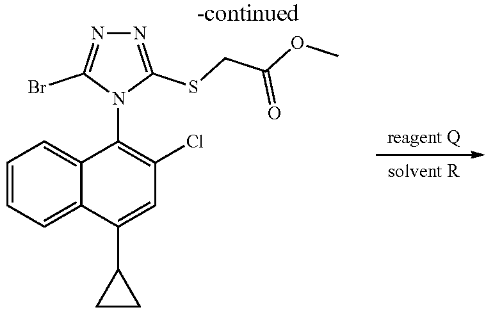

1-7

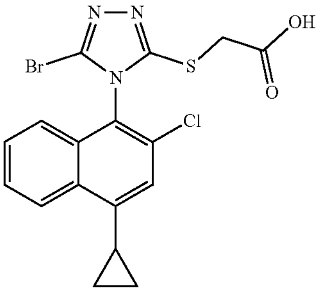
(I)

wherein, reagent A, base B and solvent C are as defined herein;

reagent D, solvent E, reagent F and solvent G are as defined herein;

base H is selected from a basic compound;

reagent I is selected from NCS;

solvent J is selected from EtOAc, DCM, PE, THF, MTBE, and $CH_3CN$;

reagent K is selected from

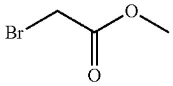
;

deacid reagent L is selected from $K_2CO_3$, $NaHCO_3$, $K_3PO_4$ and NaOAc;

solvent M is selected from EtOAc, DCM, DMF, THF and $CH_3CN$;

reagent N is selected from NBS and dibromohydantoin;

catalyst O is selected from thiocarbonyldiimidazole;

solvent P is selected from THF, $CH_3CN$ and EtOAc;

solvent Q is selected from a base; and solvent R is selected from a mixed solvent, wherein the mixed solvent is selected from a mixed solvent of tetrahydrofuran and water, a mixed solvent of methanol and water, and a mixed solvent of methanol, tetrahydrofuran and water, and the other variables are as defined herein.

In some embodiments of the present disclosure, provided is the preparation method, wherein, reagent A, base B and solvent C are as defined herein;

reagent D, solvent E, reagent F and solvent G are as defined herein;

base H is selected from NaOH;

reagent I is selected from NCS;

solvent J is selected from EtOAc;

reagent K is selected from

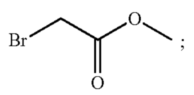

deacid reagent L is selected from NaOAc;

solvent M is selected from EtOAc;

reagent N is selected from NBS;

catalyst O is selected from thiocarbonyldiimidazole;

solvent P is selected from EtOAc;

solvent Q is selected from lithium hydroxide monohydrate; and solvent R is selected from a mixed solvent of tetrahydrofuran and pure water, and the other variables are as defined herein.

The present disclosure provides a preparation method for a compound of formula (I), (I)

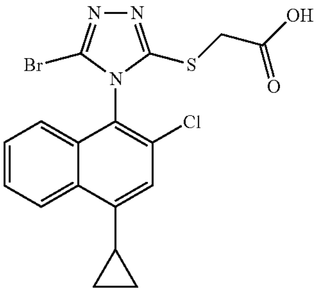

which is characterized by comprising the following step:

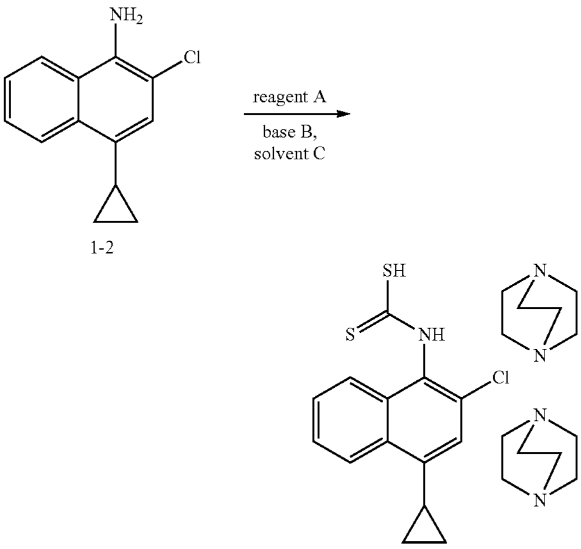

1-2

1-3 wherein, reagent A is selected from $CS_2$;

base B is selected from

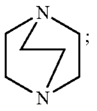

and solvent C is selected from a single solvent or a mixed solvent, wherein the single solvent is selected from n-heptane, DMF, acetone and methyl tert-butyl ether, and the mixed solvent is selected from a mixed solvent of acetone and methyl tert-butyl ether.

In some embodiments of the present disclosure, provided is the preparation method, wherein, reagent A is selected from $CS_2$;

base B is selected from

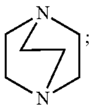

and solvent C is selected from a mixed solvent of acetone and methyl tert-butyl ether, and the other variables are as defined herein.

In some embodiments of the present disclosure, provided is the preparation method, wherein reagent A and compound 1-2 are in a molar ratio of (1-6):1, base B and compound 1-2 are in a molar ratio of (2-5):1, solvent C is a mixed solvent of methyl tert-butyl ether and acetone in a volume ratio of (15-25):1, and the other variables are as defined herein.

In some embodiments of the present disclosure, provided is the preparation method, wherein a temperature of a reaction system is controlled at 0-45° C. in the step of preparing compound 1-3A, and the other variables are as defined herein.

In some embodiments of the present disclosure, provided is the preparation method, wherein the temperature of the reaction system is controlled at 30-35° C. in the step of preparing compound 1-3A, and the other variables are as defined herein.

In some embodiments of the present disclosure, provided is the preparation method, wherein a reaction time is controlled to be 16-60 h in the step of preparing compound 1-3A, and the other variables are as defined herein.

In some embodiments of the present disclosure, the preparation method comprises the following steps:

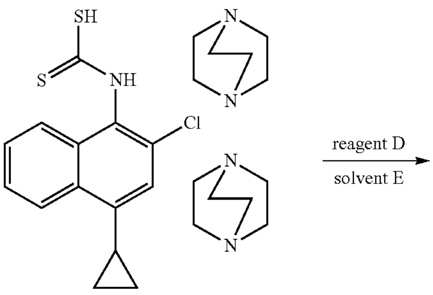

1-3

-continued

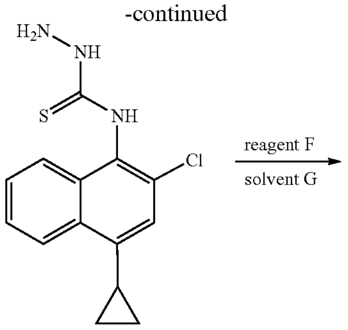

1-4

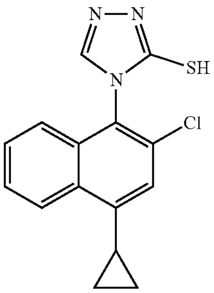

1-5 wherein, reagent D is selected from hydrazine hydrate;

solvent E is selected from EtOH, isopropanol, toluene, MTBE, THF and DMF;

reagent F is selected from DMF-DMA; and solvent G is selected from MTBE, EtOAc, n-heptane, THF, isopropanol and DMF, and the other variables are as defined herein.

In some embodiments of the present disclosure, provided is the preparation method, wherein, reagent D is selected from hydrazine hydrate;

solvent E is selected from EtOH and isopropanol;

reagent F is selected from DMF-DMA; and solvent G is selected from isopropanol, and the other variables are as defined herein.

In some embodiments of the present disclosure, provided is the preparation method, wherein reagent D and compound 1-3A are in a molar ratio of (3-15):1, reagent F and compound 1-4 are in a molar ratio of (1-3):1, and the other variables are as defined herein.

In some embodiments of the present disclosure, the preparation method comprises the following steps:

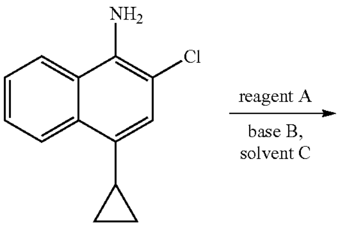

1-2

-continued

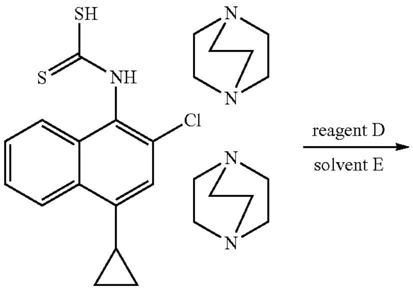

1-3

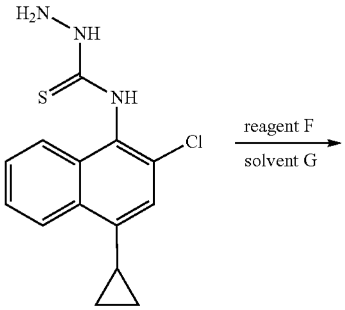

1-4

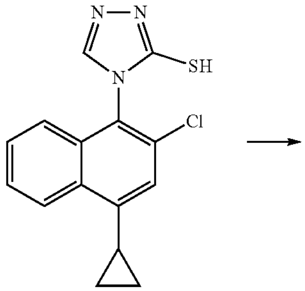

1-5

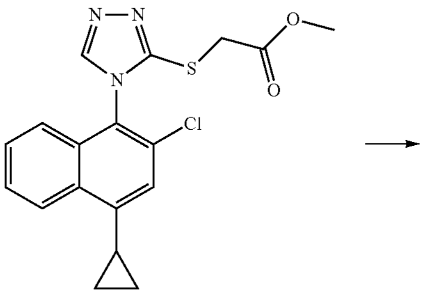

1-6

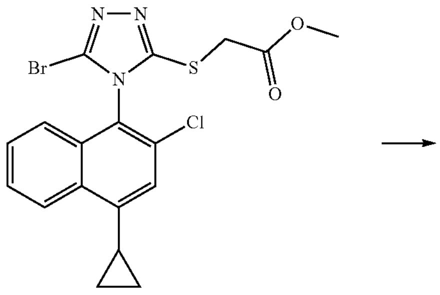

1-7

-continued
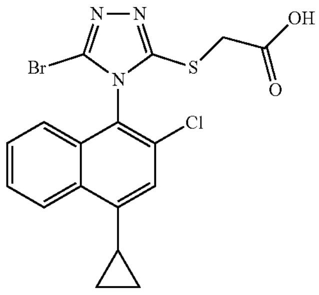
(I)
wherein,
base B is selected from
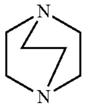
;
reagent A and solvent C are as defined herein; and
reagent D, solvent E, reagent F and solvent G are as defined herein, and the other variables are as defined herein.
In some embodiments of the present disclosure, the preparation method comprises the following steps:
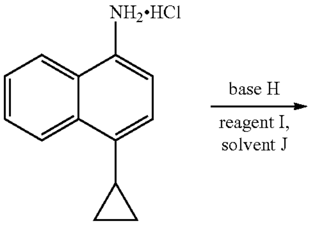
1-1
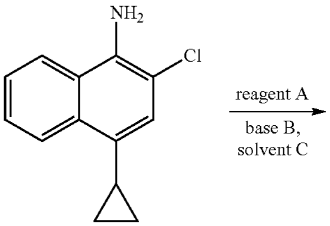
1-2
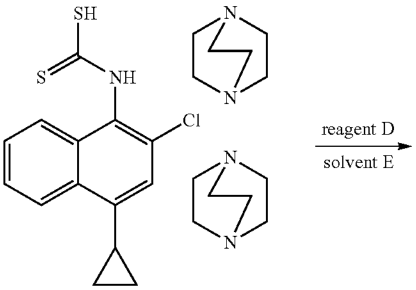
1-3
-continued
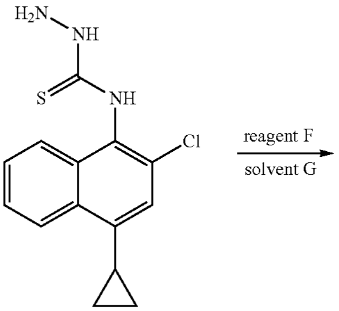
1-4
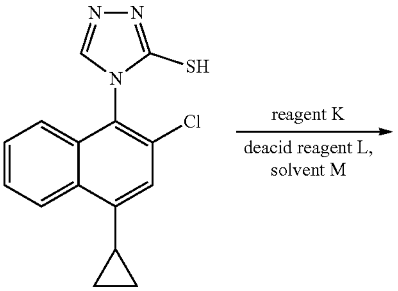
1-5
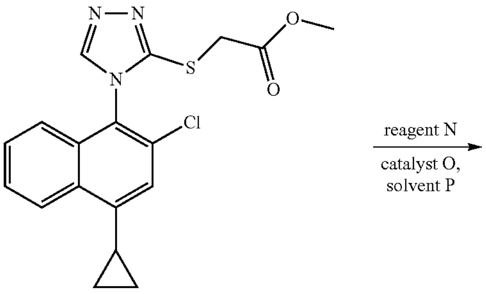
1-6
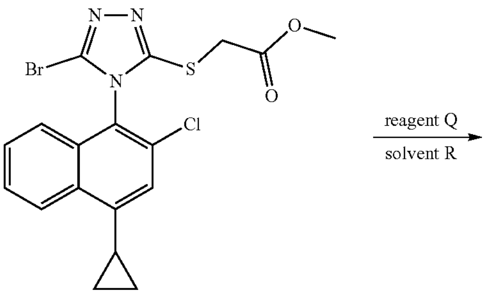
1-7
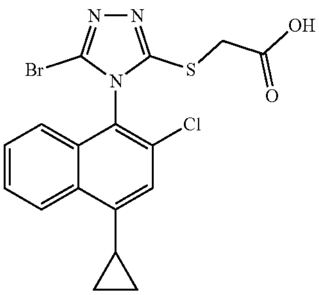
(I)

wherein, base B is selected from

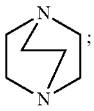

;

reagent A and solvent C are as defined herein;

reagent D, solvent E, reagent F and solvent G are as defined herein;

base H is selected from a basic compound;

reagent I is selected from NCS;

solvent J is selected from EtOAc, DCM, PE, THF, MTBE and $CH_3CN$;

reagent K is selected from

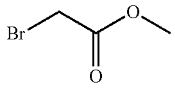

;

deacid reagent L is selected from $K_2CO_3$, $NaHCO_3$, $K_3PO_4$ and NaOAc;

solvent M is selected from EtOAc, DCM, DMF, THF and $CH_3CN$;

reagent N is selected from NBS and dibromohydantoin;

catalyst O is selected from thiocarbonyldiimidazole;

solvent P is selected from THF, $CH_3CN$ and EtOAc;

reagent Q is selected from a base; and solvent R is selected from a mixed solvent, wherein the mixed solvent is selected from a mixed solvent of tetrahydrofuran and water, a mixed solvent of methanol and water, and a mixed solvent of methanol, tetrahydrofuran and water, and the other variables are as defined herein.

In some embodiments of the present disclosure, provided is the preparation method, wherein, reagent A, base B and solvent C are as defined herein;

reagent D, solvent E, reagent F and solvent G are as defined herein;

base H is selected from NaOH;

reagent I is selected from NCS;

solvent J is selected from EtOAc;

reagent K is selected from

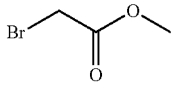

;

deacid reagent L is selected from NaOAc;

solvent M is selected from EtOAc;

reagent N is selected from NBS;

catalyst O is selected from thiocarbonyldiimidazole;

solvent P is selected from EtOAc;

reagent Q is selected from lithium hydroxide monohydrate, lithium hydroxide, sodium hydroxide and potassium hydroxide; and solvent R is selected from a mixed solvent of tetrahydrofuran and pure water in a volume ratio of (0.25-4):1, and the other variables are as defined herein.

Technical Effects

The process for synthesizing the compound of formula (I) and the intermediates thereof provided herein has the following beneficial effects: the raw materials are cheap and easy to obtain, and the defects such as difficulties in separation, purification and industrialization are overcome.

The details are as follows:

1) The raw materials used in the preparation method for the compound of formula (I) disclosed herein are conventional or common reagents, which are easy to obtain in the market and low in price, and the use of high-toxicity reagents is avoided;

2) The preparation of the compound features mild reaction conditions, ease-to-control, and simple post-treatment, a solid product is directly precipitated, and a product with higher purity can be obtained through simple recrystallization. The yield is high, and industrialization is easy to realize.

Therefore, the present disclosure has high industrial application value and economic value in the preparation of the compound of formula (I) and the intermediates thereof.

Definitions and Description

Unless otherwise stated, the following terms and phrases used in the present disclosure are intended to have the following meanings. A particular term or phrase, unless otherwise specifically defined, should not be considered as uncertain or unclear, but construed according to its common meaning. When referring to a trade name, it is intended to refer to its corresponding commercial product or its active ingredient.

The compound of the present disclosure may have a specific geometric or stereoisomeric form. All such compounds are contemplated herein, including cis and trans isomers, (−)- and (+)-enantiomers, (R)- and (S)-enantiomers, diastereoisomers, (D)-isomers, (L)-isomers, and racemic mixtures and other mixtures thereof, such as an enantiomer or diastereomer enriched mixture, all of which are encompassed within the scope of the present disclosure. Substituents such as alkyl may have an additional asymmetric carbon atom. All these isomers and mixtures thereof are encompassed within the scope of the present disclosure.

Unless otherwise stated, the term "enantiomer" or "optical isomer" refers to stereoisomers that are mirror images of each other.

Unless otherwise stated, the term "cis-trans isomer" or "geometric isomer" results from the inability of a single bond of a ring carbon atom or a double bond to rotate freely.

Unless otherwise stated, the term "diastereoisomer" refers to stereoisomers in which molecules each have two or more chiral centers and are not mirror images of each other.

Unless otherwise stated, "(+)" stands for dextrorotation, "(−)" stands for levorotation, and "(±)" stands for racemization.

Unless otherwise stated, the absolute configuration of a stereogenic center is represented by a wedged solid bond ( ) and a wedged dashed bond ( ), and the relative configuration of a stereogenic center is represented by a straight solid bond ( ) and a straight dashed bond ( ). A wavy line ( ) represents a wedged solid bond ( ) or a wedged dashed bond ( ), or a wavy line ( ) represents a straight solid bond ( ) and a straight dashed bond ( ).

Unless otherwise stated, when a double bond structure such as a carbon-carbon double bond, a carbon-nitrogen double bond, and a nitrogen-nitrogen double bond is present in the compound, and each atom on the double bond is linked to two different substituents (in the double bond including a nitrogen atom, a lone pair of electrons on the nitrogen atom is regarded as a substituent to which the nitrogen atom is linked), if the atom on the double bond of the compound and its substituents are linked using a wavy line ( ), it means that the compound exists in the form of a (Z)-type isomer, an (E)-type isomer, or a mixture of the two isomers. For example, the following formula (A) represents that the compound exists in the form of a single isomer of formula (A-1) or formula (A-2) or in the form of a mixture of both isomers of formula (A-1) and formula (A-2); the following formula (B) represents that the compound exists in the form of a single isomer of formula (B-1) or formula (B-2) or in the form of a mixture of both isomers of formula (B-1) and formula (B-2); and the following formula (C) represents that the compound exists in the form of a single isomer of formula (C-1) or formula (C-2) or in the form of a mixture of both isomers of formula (C-1) and formula (C-2).

(A)

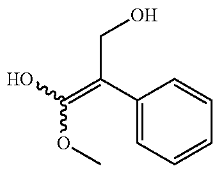

(A-1)

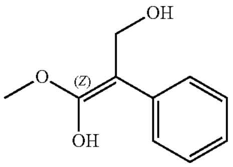

(A-2)

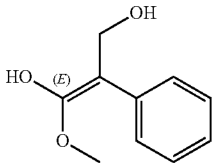

(B)

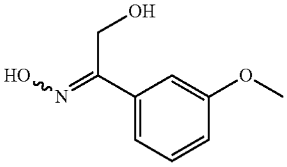

(B-1)

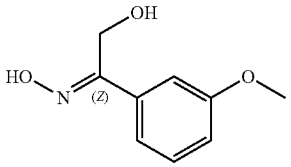

-continued (B-2)

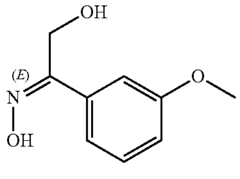

(C)

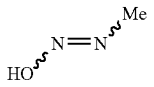

(C-1)

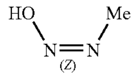

(C-2)

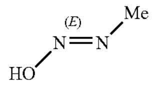

Unless otherwise stated, the term "isomeric excess" or "enantiomeric excess" refers to the difference between the relative percentages of two isomers or enantiomers. For example, if the content of one isomer or enantiomer is 90% and the content of the other isomer or enantiomer is 10%, the isomeric or enantiomeric excess (ee) is 80%.

The compound of the present disclosure may contain an unnatural proportion of atomic isotope at one or more of the atoms that constitute the compound. For example, the compound may be labeled with a radioisotope, such as tritium ($^{3}$H), iodine-125 ($^{125}$1), or C-14 ($^{14}$C). For another example, hydrogen can be substituted by deuterium to form a deuterated drug, and the bond formed by deuterium and carbon is firmer than that formed by common hydrogen and carbon. Compared with an un-deuterated drug, the deuterated drug has the advantages of reduced toxic side effect, increased stability, enhanced efficacy, and prolonged biological half-life and the like. All isotopic variations of the compounds of the present disclosure, whether radioactive or not, are encompassed within the scope of the present disclosure.

The intermediate compounds of the present disclosure can be prepared by a variety of synthetic methods well known to those skilled in the art, including the specific embodiments listed below, embodiments formed by combinations thereof with other chemical synthetic methods, and equivalent substitutions thereof known to those skilled in the art. Preferred embodiments include, but are not limited to, the examples of the present disclosure.

The chemical reactions of the specific embodiments of the present disclosure are carried out in a suitable solvent that must be suitable for the chemical changes in the present disclosure and the reagents and materials required. In order to obtain the compounds of the present disclosure, it is sometimes necessary for those skilled in the art to modify or select a synthesis procedure or a reaction scheme based on the existing embodiments.

The present disclosure is described in detail below by way of examples, which are not intended to limit the present disclosure in any way.

The solvents used in the present disclosure can be commercially available. The following abbreviations are used in the present disclosure:

| | |
|---|---|
| DMF-DMA | N,N-Dimethylformamide dimethyl acetal |
| DCM | Dichloromethane |
| THF | Tetrahydrofuran |
| DMF | N,N-Dimethylformamide |
| DMSO | Dimethyl sulfoxide |
| EtOH | Ethanol |
| TEA | Triethanolamine |
| DBU | 1,8-Diazabicycloundec-7-ene |
| $CS_2$ | Carbon disulfide |
| DIPEA | N,N-Diisopropylethylamine |
| MTBE | Methyl tert-butyl ether |
| EtOAc | Ethyl acetate |
| $CH_3CN$ | Acetonitrile |
| $K_2CO_3$ | Potassium carbonate |
| $NaHCO_3$ | Sodium bicarbonate |
| $K_3PO_4$ | Potassium phosphate |
| NCS | N-Chlorosuccinimide |
| PE | Petroleum ether |
| NaOAc | Sodium acetate |
| NBS | N-Bromosuccinimide |

Compounds are named according to conventional nomenclature rules in the art or using ChemDraw® software, and supplier's catalog names are given for commercially available compounds.

DETAILED DESCRIPTION OF THE PREFERRED EMBODIMENT

In order to better understand the content of the present disclosure, further description is given with reference to specific examples, but the specific embodiments are not intended to limit the content of the present disclosure.

Example 1: Preparation of Compound of Formula (I)

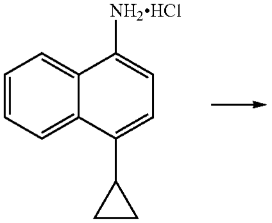

1-1

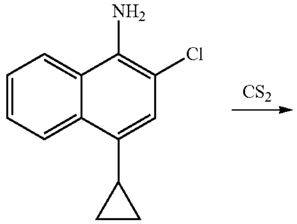

1-2

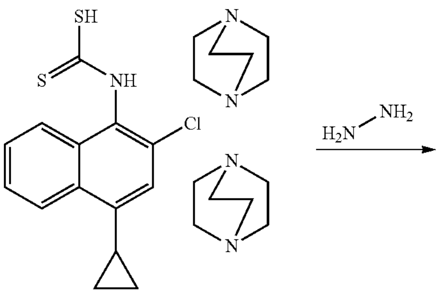

1-3

-continued

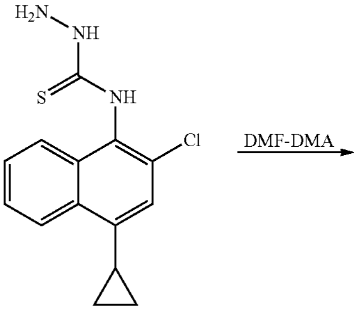

1-4

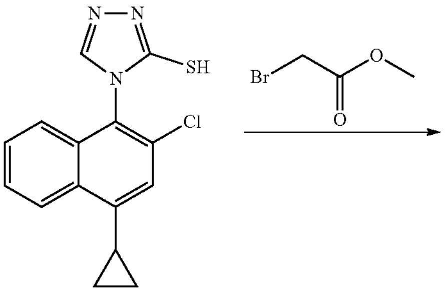

1-5

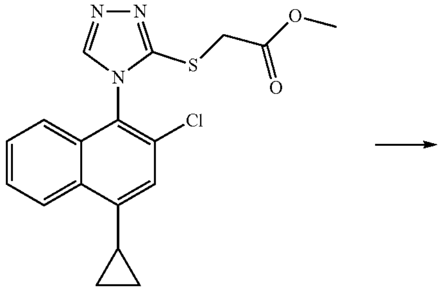

1-6

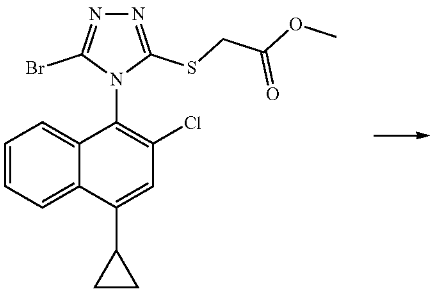

1-7

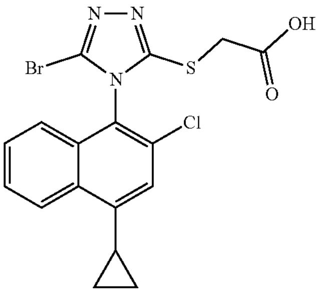

(I)

Step 1: Synthesis of Compound 1-2

Compound 1-1 (1.0 kg, 4.55 mol, 1 eq) was added to 5.0 L of water, the resulting mixture was adjusted to pH of about 10 with a 2 M aqueous NaOH solution, and then extracted with 5.0 L of ethyl acetate. The organic phases were dried over anhydrous sodium sulfate and filtered. The filter cake was washed with 2.0 L of ethyl acetate. The mother liquors were combined and concentrated under reduced pressure to obtain a free 1-1. At an external temperature of 25-30° C., the free 1-1 was dissolved in ethyl acetate (5.0 L), and then N-chlorosuccinimide (668.32 g, 5.01 mol, 1.1 eq) was added in batches. After the addition was completed, the internal temperature was raised to 40-45° C. The resulting reaction solution was further stirred for 12 h. As the reaction proceeded, the internal temperature slowly dropped to 25-30° C. The reaction solution was filtered through celite, and a mother liquor was collected. 7.0 L of a 10% aqueous sodium bisulfite solution was added to the mother liquor, the resulting mixture was stirred for 15 min, and the liquids were separated. The organic phase was further washed twice with 7.0 L of a 10% aqueous sodium bisulfite solution. The resulting organic phase was then washed once with water (7.0 L), washed once with a saturated aqueous sodium chloride solution (7.0 L), dried over anhydrous sodium sulfate (1 kg), and filtered. The filtrate was concentrated under reduced pressure to obtain compound 1-2 (896.36 g, 90.47% yield). $^1$H NMR (400 MHz, $CDCl_3$) δ: 8.41-8.35 (m, 1H), 7.85-7.80 (m, 1H), 7.57-7.52 (m, 2H), 7.19 (d, J=0.8 Hz, 1H), 4.43 (s, 2H), 2.26-2.17 (m, 1H), 1.07-0.97 (m, 2H), 0.74-0.67 (m, 2H); MS m/z: 217.9 $[M+H]^+$.

Step 2: Synthesis of Compound 1-3

Compound 1-2 (650.00 g, 2.98 mol, 1 eq) was dissolved in a mixed solvent of methyl tert-butyl ether and acetone (6.5 L, V:V=95:5) at 25-30° C., and then carbon disulfide (1134.49 g, 14.9 mol, 5 eq) and triethylene diamine (1002.79 g, 8.94 mol, 3 eq) were added sequentially with stirring. The resulting reaction solution was stirred at 30-35° C. for 48 h. After the reaction was completed, the stirring was continued, and the reaction solution was programmed-cooled to 0° C. (the cooling rate was controlled at 5° C./h). The suspension was filtered, and the filter cake was washed twice with 100 mL of a mixed solvent of methyl tert-butyl ether and acetone (methyl tert-butyl ether:acetone=95:5, v:v), and dried in vacuum to obtain compound 1-3 as a light yellow solid (1345.68 g, 90.51% yield). $^1$H NMR (400 MHz, DMSO-$d_6$) δ: 9.86 (br s, 1H), 8.37-8.31 (m, 1H), 7.93-7.85 (m, 1H), 7.59-7.51 (m, 2H), 7.20 (s, 1H), 3.82 (br s, 24H), 2.45-2.35 (m, 1H), 1.11-1.01 (m, 2H), 0.80-0.71 (m, 2H).

Step 3: Synthesis of Compound 1-4

Compound 1-3 (530.0 g, 0.97 mol, 1 eq) and 3.5 L of ethanol (EtOH) were added to a reaction flask. The resulting mixture was stirred, and hydrazine hydrate (248.34 g, 4.86 mol, 5 eq) was added dropwise at 20-23° C. After the dropwise addition was completed, the resulting mixed solution was stirred at 20-23° C. for 18 h, followed by addition of hydrazine hydrate (12 mL). The resulting reaction solution was further stirred at 20-23° C. for 48 h, and then filtered. The filter cake was washed twice with 100 mL of ethanol. The washed filter cake was collected and dried in a vacuum drying oven at 35° C. to obtain compound 1-4 (271.82 g, 90.05% yield). $^1$H NMR (400 MHz, DMSO-$d_6$) δ: 9.22 (br s, 1H), 8.48-8.31 (m, 1H), 7.91-7.75 (m, 1H), 7.67-7.48 (m, 2H), 7.27 (s, 1H), 2.80 (s, 2H), 2.47-2.40 (m, 1H), 1.12-1.08 (m, 2H), 0.85-0.71 (m, 2H); MS m/z: 291.9 $[M+H]^+$.

Step 4: Synthesis of Compound 1-5

To a reaction flask were sequentially added 1-4 (260.0 g, 0.89 mol, 1 eq), isopropanol (1.3 L) and N,N-dimethylformamide dimethyl acetal (159.26, 1.34 mol, 1.5 eq), and the resulting mixture solution was stirred at 60° C. for 16 h. The reaction solution was concentrated under reduced pressure to about 500 mL, cooled to room temperature, and adjusted to pH=5-6 with a diluted aqueous hydrochloric acid solution (1 M). The resulting reaction solution was further stirred for 2 h, and then filtered. The filter cake was washed with 200 mL of filtered mother liquor. The washed filter cake was collected and dried in vacuum to obtain a light grey solid. The solid was stirred and slurried with 2.0 L of n-heptane, and the resulting slurry was stirred at 20-25° C. for 16 h, and filtered. The filter cake was washed twice with n-heptane (200 mL). The washed filter cake was collected and dried under reduced pressure to obtain compound 1-5 (210.68 g, 83.35% yield). $^1$H NMR (400 MHZ, $CD_3OD$) δ: 8.58 (d, J=8.0 Hz, 1H), 8.37 (s, 1H), 7.73-7.67 (m, 1H), 7.67-7.62 (m, 1H), 7.48-7.45 (m, 1H), 7.38-7.34 (m, 1H), 2.59-2.49 (m, 1H), 1.25-1.18 (m, 2H), 0.96-0.84 (m, 2H); MS m/z: 301.9 $[M+H]^+$.

Step 5: Synthesis of Compound 1-6

To a 5 L three-necked flask were sequentially added compound 1-5 (330.02 g) and ethyl acetate (3.3 L), and the resulting mixture was stirred homogeneously. Sodium acetate (179.68 g) was then added in one portion, and the resulting mixture was stirred homogeneously. Subsequently, methyl bromoacetate (200.86 g) was added in one portion, and the resulting mixture was stirred homogeneously. The resulting reaction solution was stirred and reacted at an external temperature of 60° C. for 16 h, then filtered (at an external temperature of 60° C.) while it was still hot. The filter cake was washed twice with ethyl acetate (100 mL), and the filtrates were combined. Four batches (of the same mass) were fed in parallel by the same process, and the ethyl acetate filtrates obtained by filtration after the reaction was completed were combined and treated in the following manner.

Washing for the first time: 14 L of pure water was added to the above ethyl acetate filtrate. The resulting mixture was vigorously stirred for 20 min, and then left standing for separation. After the separation, the aqueous phase was discharged, and a small amount of flocculent layer remained in the ethyl acetate phase.

Washing for the second time: 14 L of pure water was then added to the ethyl acetate phase. The resulting mixture was vigorously stirred for 20 min, and then left standing for separation. After the separation, the aqueous phase was discharged, and a small amount of flocculent layer remained in the ethyl acetate phase.

Washing for the third time: 14 L of pure water was then added to the ethyl acetate phase. The resulting mixture was vigorously stirred for 20 min, and then left standing for separation. After the separation, the lower aqueous phase was discharged. The lower organic phase containing a small amount of floccule was filtered through celite, combined with the remaining organic phase (about 14 L in total), dried over anhydrous sodium sulfate (5 kg), and filtered. The filtrate was concentrated under reduced pressure to obtain a dark red oil, which was then left standing and cooled to room temperature to obtain a crude product of 1-6 as a dark red solid (1640.73 g, 87.11% yield). $^1H$ NMR (400 MHz, DMSO-$d_6$) δ: 8.94 (s, 1H), 8.58 (d, J=8.0 Hz, 1H), 7.84-7.66 (m, 2H), 7.52 (s, 1H), 7.12 (d, J=8.0 Hz, 1H), 4.16-4.05 (m, 2H), 3.63 (s, 3H), 2.66-2.56 (m, 1H), 1.23-1.11 (m, 2H), 1.01-0.83 (m, 2H); MS m/z: 374.0 $[M+H]^+$.

Step 6: Synthesis of Compound 1-7

To a 5 L three-necked flask were sequentially added compound 1-6 (330.05 g) and ethyl acetate (3.3 L). The resulting mixed solution was stirred at an external temperature of 40-45° C. until completely dissolved. Thiocarbonyldiimidazole (15.73 g) was added with stirring, and the resulting mixture was further stirred at an external temperature of 40-45° C. for 10 min. N-Bromosuccinimide (157.10 g) was added in batches with stirring, and the resulting reaction solution was further stirred at an external temperature of 40-45° C. for 1 h. Finally, N-bromosuccinimide (15.74 g) was added, and the resulting reaction solution was further stirred at an external temperature of 40-45° C. for 15 min, then cooled to room temperature and filtered through celite. The filter cake was washed twice with ethyl acetate (200 mL), and the filtrates were combined. Five batches (of the same mass) were fed in parallel by the same process, and the ethyl acetate filtrates obtained by filtration after the reaction was completed were combined and then treated in the following manner.

Washing for the first time: 17.2 L of pure water was added to the above ethyl acetate filtrate. The resulting mixture was vigorously stirred for 20 min, and then left standing for separation. After the separation, the aqueous phase was discharged, and a small amount of flocculent layer remained in the ethyl acetate phase.

Washing for the second time: 17.2 L of a 10% sodium bisulfite solution was then added to the ethyl acetate phase. The resulting mixture was vigorously stirred for 20 min, and then left standing for separation. After the separation, the aqueous phase was discharged, and a small amount of flocculent layer remained in the ethyl acetate phase.

Washing for the third time: 17.2 L of a 10% sodium bisulfite solution was then added to the ethyl acetate phase. The resulting mixture was vigorously stirred for 20 min, and then left standing for separation. After the separation, the aqueous phase was discharged, and a small amount of flocculent layer remained in the ethyl acetate phase.

Washing for the fourth time: 17.2 L of pure water was added to the above ethyl acetate filtrate. The resulting mixture was vigorously stirred for 20 min, and then left standing for separation. After the separation, the aqueous phase was discharged, and a small amount of flocculent layer remained in the ethyl acetate phase.

Washing for the fifth time: 17.2 L of pure water was added to the above ethyl acetate filtrate. The resulting mixture was vigorously stirred for 20 min, and then left standing for separation. After the separation, the lower aqueous phase was discharged. The lower organic phase containing a small amount of floccule was filtered through celite, combined with the remaining organic phase (about 17 L in total), and dried over anhydrous sodium sulfate (8 kg). The desiccant was removed by filtration, and the filtrate was concentrated under reduced pressure to obtain a crude product as a dark red solid (1562.17 g).

The above dark red solid was added to methyl tert-butyl ether (5.5 L), and the resulting mixture was stirred at an external temperature of 80° C. until it became clear. To the methyl tert-butyl ether solution was further added n-heptane (3.5 L). The resulting mixed solution was stirred at an external temperature of 60° C. for 16 h, and a large amount of solid was then precipitated in the solution. Then n-heptane (2.0 L) was added. The resulting mixed solution was further stirred at an external temperature of 60° C. for 2 h, and then programmed-cooled to an external temperature of 40° C. (5° C./h). The stirring was stopped, and then filtration was performed. The filter cake was washed thoroughly with n-heptane (1.5 L). The washed filter cake was collected and dried in vacuum at 40° C. for 2 h to obtain a light yellow solid (1107.09 g).

The above light yellow solid (1100.01 g) was added to isopropanol (5.5 L), and the resulting mixture was heated to an external temperature of 110° C. and refluxed to obtain a clear solution. The isopropanol solution was programmed-cooled to an external temperature of 95° C. (5° C./h), and further stirred at this temperature for 16 h. A small amount of off-white solid was precipitated. The resulting mixture was further programmed-cooled to an external temperature of 60° C. (5° C./h), and further stirred at this temperature for 60 h. A large amount of solid was precipitated. The resulting mixture was filtered while it was still hot, and the filter cake was washed thoroughly with isopropanol (500 mL). The washed filter cake was collected and dried in vacuum at 40° C. for 16 h to obtain 1-7 as a light yellow solid (962.69 g, 52.27% yield). $^1H$ NMR (400 MHz, $CD_3OD$) δ: 8.63 (d, J=8.3 Hz, 1H), 7.82-7.65 (m, 2H), 7.51 (s, 1H), 7.29-7.20 (m, 1H), 4.16-3.94 (m, 2H), 3.72 (s, 3H), 2.64-2.49 (m, 1H), 1.30-1.20 (m, 2H), 0.99-0.85 (m, 2H); MS m/z: 453.7 $[M+H+2]^+$.

Step 7: Synthesis of Compound of Formula (I)

To a 5 L three-necked flask were sequentially added compound 1-7 (330.12 g) and a mixed solution of anhydrous tetrahydrofuran (1650 mL) and pure water (1650 mL), and the resulting mixture was stirred homogeneously. Lithium hydroxide monohydrate (183.91 g) was then added in one portion, and the resulting reaction solution was stirred at an external temperature of 30° C. for 2 h. After the reaction was completed, the reaction solution was cooled to room temperature (20° C.). Three batches were fed in parallel by the same process. The reaction solutions were combined and treated in the following manner.

The combined reaction solution was concentrated under reduced pressure (<40° C.) to remove tetrahydrofuran, and the aqueous phase was cooled to 0° C. At 0° C., an aqueous hydrobromic acid solution (40%) was added dropwise with stirring until the pH of the mixed solution was 3, and a large amount of solid was precipitated. The mixture was further stirred at an external temperature of 20° C. for 16 h, and pH=3 was redetermined. The mixture was filtered, and the filter cake was washed thoroughly with pure water (500 mL). The washed filter cake was collected and dried in vacuum at 40° C. for 6 h to obtain a crude product of the compound of formula (I) (895.65 g). To a 10 L three-necked flask were sequentially added the crude product of the compound of formula (I) (890.12 g) and a mixed solution of ethanol (2225 mL) and pure water (2225 mL), and the resulting mixture was stirred at an external temperature of 40° C. for 48 h, programmed-cooled to an external temperature of 20° C. (5° C./h), and then filtered. The filter cake was washed thoroughly with a mixed solution of ethanol and pure water (450 mL, V:V=1:1). The washed filter cake was collected and dried in vacuum at 40° C. for 16 h to obtain the compound of formula (I) (692.16 g, 77.78% yield). $^1H$ NMR (400 MHz, DMSO-$d_6$) δ: 13.02 (s, 1H), 8.61 (d, J=8.4 Hz, 1H), 7.83-7.69 (m, 2H), 7.56 (d, J=8.0 Hz, 1H), 7.19 (d, J=8.4 Hz, 1H), 4.12-3.96 (m, 2H), 2.69-2.57 (m, 1H), 1.24-1.13 (m, 2H), 1.03-0.91 (m, 2H); MS m/z: 439.9 $[M+H+2]^+$.

What is claimed is:

1. A preparation method for a compound of formula 1-3A, wherein, the method comprises the following step:

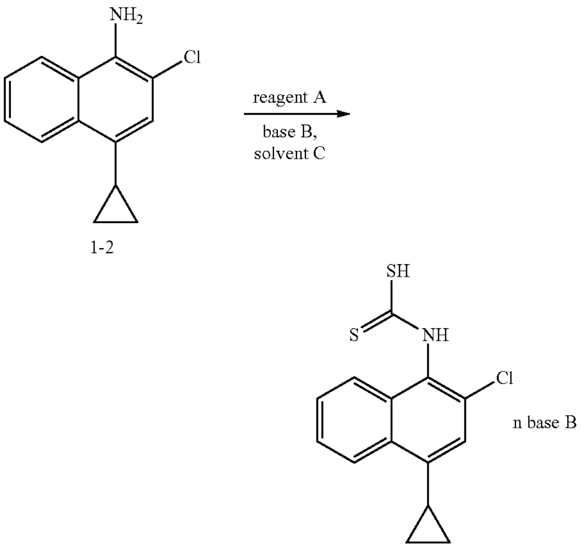

1-2

1-3A wherein, n is selected from 0, 1 and 2;

reagent A is $CS_2$;

base B is selected from TEA, DBU, DIPEA and

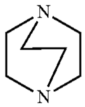;

and solvent C is selected from a single solvent or a mixed solvent, wherein the single solvent is selected from n-heptane, DMF, acetone and methyl tert-butyl ether, and the mixed solvent is a mixed solvent of acetone and methyl tert-butyl ether.

2. The preparation method according to claim 1, wherein base B is

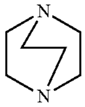;

and solvent C is selected from a single solvent or a mixed solvent, wherein the single solvent is methyl tert-butyl ether, and the mixed solvent is a mixed solvent of acetone and methyl tert-butyl ether.

3. The preparation method according to claim 2, wherein solvent C is a mixed solvent of acetone and methyl tert-butyl ether.

4. The preparation method according to claim 1, wherein reagent A and compound 1-2 are in a molar ratio of (1-6):1, base B and compound 1-2 are in a molar ratio of (2-5):1, and solvent C is a mixed solvent of methyl tert-butyl ether and acetone in a volume ratio of (15-25):1.

5. The preparation method according to claim 1, wherein a temperature of a reaction system is controlled at 0-45° C. in the step of preparing compound 1-3A.

6. The preparation method according to claim 5, wherein the temperature of the reaction system is controlled at 30-35° C. in the step of preparing compound 1-3A.

7. The preparation method according to claim 1, wherein a reaction time is controlled to be 16-60 h in the step of preparing compound 1-3A.

8. A preparation method for a compound of formula 1-5, wherein the compound of formula 1-3A is prepared as in claim 1, and the preparation method comprises the following steps:

1-3A

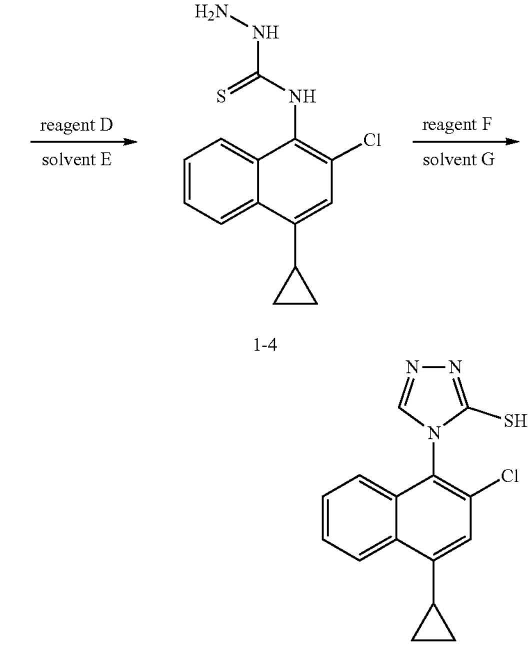

1-4

1-5 wherein, reagent D is hydrazine hydrate;

solvent E is selected from EtOH, isopropanol, toluene, MTBE, THF and DMF;

reagent F is DMF-DMA; and solvent G is selected from MTBE, EtOAc, n-heptane, THF, isopropanol and DMF.

9. The preparation method according to claim 8, wherein solvent E is selected from EtOH and isopropanol;

and solvent G is isopropanol.

10. The preparation method according to claim 9, wherein reagent D and compound 1-3A are in a molar ratio of (3-15):1, and reagent F and compound 1-4 are in a molar ratio of (1-3):1.

11. A preparation method for a compound of formula (I), wherein the compound of formula 1-3A is prepared as in claim 1, and the preparation method comprises the following steps:

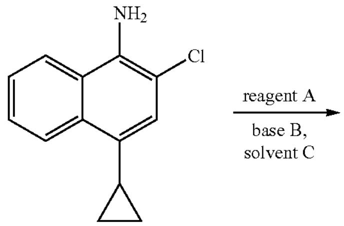
1-2
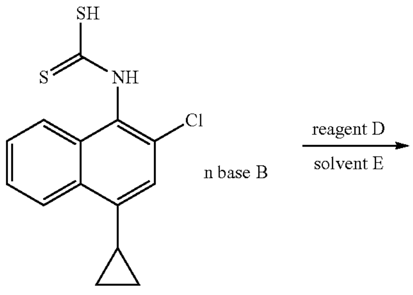
1-3A
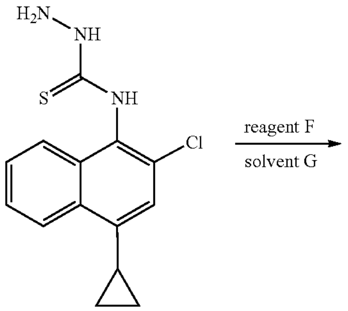
1-4
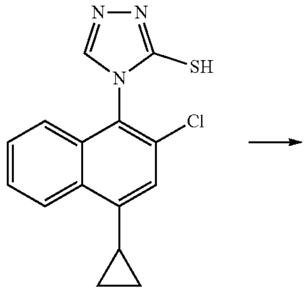
1-5
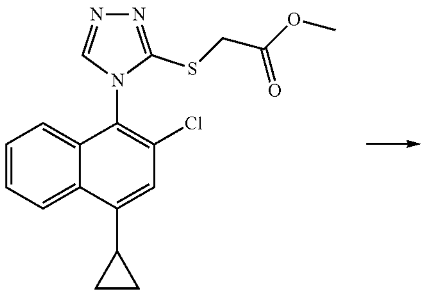
1-6
-continued
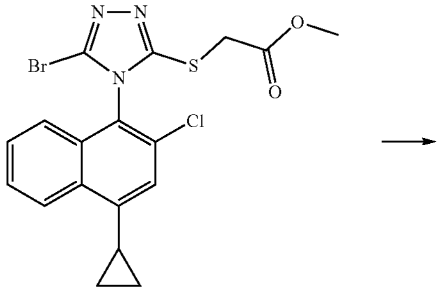
1-7
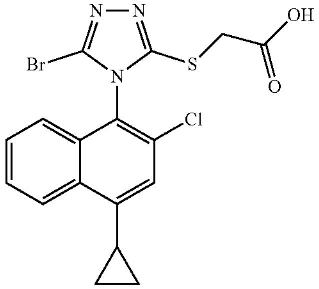
(I)
wherein,
reagent D is hydrazine hydrate;
solvent E is selected from EtOH and isopropanol;
reagent F is DMF-DMA; and
solvent G is isopropanol.
12. The preparation method according to claim 11, comprising the following steps:
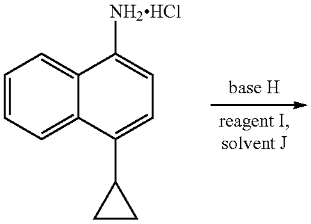
1-1
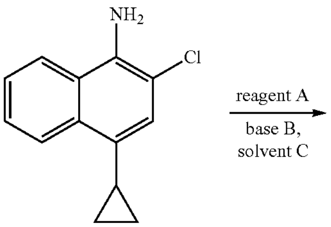
1-2

-continued

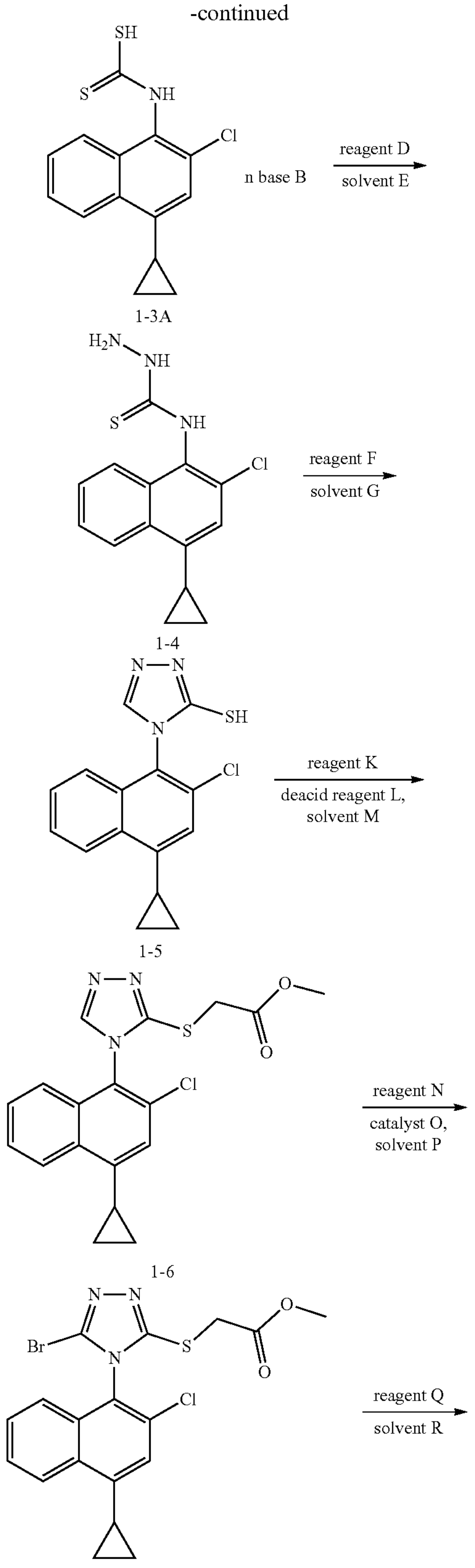

1-3A 1-4

1-5

1-6

1-7

-continued

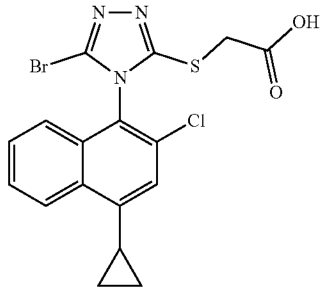

(I)

wherein, base H is a basic compound;

reagent I is NCS;

solvent J is selected from EtOAc, DCM, PE, THE, MTBE, and $CH_3CN$;

reagent K is

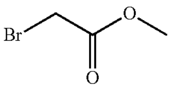

;

deacid reagent L is selected from $K_2CO_3$, $NaHCO_3$, $K_3PO_4$ and NaOAc;

solvent M is selected from EtOAc, DCM, DMF, THF and $CH_3CN$;

reagent N is selected from NBS and dibromohydantoin;

catalyst O is thiocarbonyldiimidazole;

solvent P is selected from THE, $CH_3CN$ and EtOAc;

reagent Q is a base; and solvent R is selected from a mixed solvent, wherein the mixed solvent is selected from a mixed solvent of tetrahydrofuran and water, a mixed solvent of methanol and water, and a mixed solvent of methanol, tetrahydrofuran and water.

13. The preparation method according to claim 12, wherein base H is NaOH;

solvent J is EtOAc;

deacid reagent L is NaOAc;

solvent M is EtOAc;

reagent N is NBS;

solvent P is EtOAc;

reagent Q is selected from lithium hydroxide monohydrate, lithium hydroxide, sodium hydroxide and potassium hydroxide; and solvent R is selected from a mixed solvent of tetrahydrofuran and pure water in a volume ratio of (0.25-4):1.

* * * * *